United States Patent
Derda et al.

(10) Patent No.: US 12,416,101 B2
(45) Date of Patent: Sep. 16, 2025

(54) GENETICALLY-ENCODED MACROCYCLIC PEPTIDE LIBRARIES BEARING A PHARMACOPHORE

(71) Applicant: THE GOVERNORS OF THE UNIVERSITY OF ALBERTA, Edmonton (CA)

(72) Inventors: Ratmir Derda, Edmonton (CA); Raja Mukherjee, Edmonton (CA); Arunika Ekanayake, Edmonton (CA)

(73) Assignee: 48Hour Discovery Inc., Edmonton (CA)

( * ) Notice: Subject to any disclaimer, the term of this patent is extended or adjusted under 35 U.S.C. 154(b) by 794 days.

(21) Appl. No.: 17/294,815

(22) PCT Filed: Nov. 28, 2019

(86) PCT No.: PCT/CA2019/051703
§ 371 (c)(1),
(2) Date: May 18, 2021

(87) PCT Pub. No.: WO2020/107118
PCT Pub. Date: Jun. 4, 2020

(65) Prior Publication Data
US 2022/0002341 A1    Jan. 6, 2022

Related U.S. Application Data

(60) Provisional application No. 62/772,339, filed on Nov. 28, 2018.

(51) Int. Cl.
*C40B 40/10*    (2006.01)
*C07K 1/04*    (2006.01)
(Continued)

(52) U.S. Cl.
CPC .............. *C40B 40/10* (2013.01); *C07K 1/047* (2013.01); *C40B 40/02* (2013.01); *C40B 50/06* (2013.01); *C40B 70/00* (2013.01)

(58) Field of Classification Search
None
See application file for complete search history.

(56) References Cited

U.S. PATENT DOCUMENTS 7,622,248 B2    11/2009    Suga et al.
2017/0355982 A1*    12/2017    Derda ................ C12N 15/1037

FOREIGN PATENT DOCUMENTS

| WO | 2012074130 | 6/2012 |
| WO | 2016061695 | 4/2016 |
| WO | 2020107118 | 6/2020 |

OTHER PUBLICATIONS

Franzini et al, DNA-Encoded Chemical Libraries: Advancing beyond Conventional Small-Molecule Libraries Accounts of Chemical Research, Journal, Acc Chem Res, 2014, 47, 1247- 1255.
(Continued)

*Primary Examiner* — Christian C Boesen
(74) *Attorney, Agent, or Firm* — Bennett Jones LLP

(57) ABSTRACT

The present invention relates to a method of forming a macrocyclic peptide bearing a pharmacophore and said produced macrocyclic peptide, wherein the method comprises the steps of: reacting a peptide with two thiol groups of cysteine side chains with the reactive compound 1,5-dichloropentanedion-2,4. The reaction between the reactive compound and the peptide produces an 1,3-diketone-containing macrocyclic polypeptide. The macrocycle with a 1,3-diketone group is then modified by reaction of said macrocycle with an alkyl or aryl hydrazine group bearing a pharmacophore in benign aqueous conditions. The macrocycles may be displayed in a library, such as a phage display
(Continued)

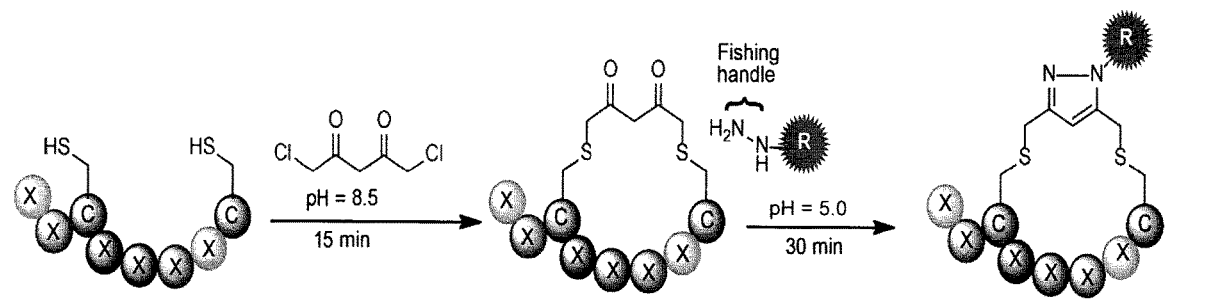

Unprotected peptide
X = any natural amino acids

R = Affinity/Fluorescent/Bioorthogonal handle/Sugartag

● Aqueous ● Fast ● Benign ● Biocompatible library, and used to biopan for affinity against a selected target.

7 Claims, 10 Drawing Sheets

(51) Int. Cl.
    *C40B 40/02*     (2006.01)
    *C40B 50/06*     (2006.01)
    *C40B 70/00*     (2006.01)

(56) References Cited

OTHER PUBLICATIONS

Assem et al, Acetone-Linked Peptides: A Convergent Approach for Peptide Macrocyclization and Labeling, Journal, Angew Chem Int, 2015, 54, 8665-8668.

Ng et al, Phage-displayed macrocyclic glycopeptide libraries, Journal, Org Biomol Chem, 2016, 14, 5539-5545.

McCarthy et al., Phage Display of Dynamic Covalent Binding Motifs Enables Facile Development of Targeted Antibiotics, Journal, J Am Chem Soc, 2018, 140, 6137-6145.

Uematsu et al., Combinatorially Screened Peptide as Targeted Covalent Binder: Alteration of Bait-Conjugated Peptide to Reactive Modifier, Journal, Bioconjugate Chem, 2018, 29, 1866-1871.

Gupta et al, Reactivity, Selectivity, and Stability in Sulfenic Acid Detection: A Comparative Study of Nucleophilic and Electrophilic Probes, Journal, Bioconjugate Chem, 2016, 27, 1411-1418.

Rader et al, A Humanized Aldolase Antibody for Selective Chemotherapy and Adaptor Immunotherapy, Journal, Journal of Molecular Biology, 2003, 332, 889-899.

Barbas et al, Assembly of combinatorial antibody libraries on phage surfaces: the gene III site, Journal, PNAS, 1991, 88, 7978-7982.

\* cited by examiner

GENETICALLY-ENCODED MACROCYCLIC PEPTIDE LIBRARIES BEARING A PHARMACOPHORE

FIELD

The present application relates generally to the field of drug discovery using genetically encoded macrocyclic peptide libraries.

BACKGROUND

Drug discovery continues to be a difficult process. Increased effort in pharmaceutical research and development have not led to an attendant rise in new drugs, despite a plethora of new targets, as genomic and proteomic studies continue to report the association of one or more genes or proteins to a disease state. New chemical entities to interrogate this myriad of targets are needed. Combinatorial chemistry permitted a significant advance in the identification of novel therapeutic molecules. Although successful to some degree with associated techniques, such as parallel synthesis, solid phase methodology, high-throughput compound profiling and purification, adoption of new chemical technologies has been limited.

There has also been a shift in drug discovery approaches towards biological entities, leading to a greater number of antibody and protein drug products appearing and advancing in the pipelines of pharmaceutical and biotech companies. Unfortunately, attempts to modulate intracellular pathways and targets that are inaccessible to biologics have also proven inaccessible to small molecules.

The limitations of biological molecules coupled with the difficulties encountered with small molecules has led to consideration of non-traditional structures for modulation of these challenging targets, such as protein-protein interactions (PPI), protein-nucleic acid interactions and transcription factors. One particularly attractive chemical class that suits this purpose has been macrocyclic compounds.

Macrocycle libraries have been produced that contain an unnatural chemotype by reacting a phage-displayed library with two cysteines and dichloroacetone-derived oxime. The oxime bond is known to have limited hydrolytic stability. Forming the oxime requires prolonged incubation in acidic conditions and presence of toxic catalyst that can be detrimental to integrity of a genetically-encoded library, such as a phage library.

Macrocyclic libraries with an azido or alkyne group are known. Modification of the azido or alkyne groups can introduce an unnatural pharmacophore into the cyclic peptide. It is also known that reaction for modification of said azido or alkyne groups requires presence of redox active metals, such as copper, which are known to destroy the integrity of nucleic acids via radical oxidative processes (e.g., Fenton reaction).

Fragment based design (FBD) is a powerful method for development of ligands for any proteins starting from weak, promiscuous fragments A and B that bind to the protein. Two-fragment combination A-B that binds with higher affinity and specificity when compared to the original fragments are identified. Genetically-encoded fragment based discovery (GE-FBD), explores a similar concept, in which one of the fragment is a linear peptide or peptide macrocycle. Several examples of GE-FBD have been reported and reviewed.[1] However, GE-FBD methods do not provide rapid and robust introduction of fragments into peptide libraries via irreversible covalent bonds. Methods that introduce the fragment and change the topology to macrocyclic are the most attractive.

Dichloroacetone linchpin[2] can convert linear peptide to cyclic and simultaneously introduce ketone functionality into the peptide library. However, late-stage functionalization of ketone-macrocycle is slow, requiring up to 24 hours of incubation in acidic conditions, which is detrimental to phage viability. This deficiency can be bypassed by pre-functionalization of dichloroacetone to form dichlorooximes and introduce a diverse range of glycans into peptide macrocycles.[3]

Two-step reduction of disulfides and alkylations of Cys to introduce boroxazole functionalities into commercially available phage displayed PhD C7C library has been demonstrated.[4] A similar cysteine alkylation to introduce non-covalent and covalent warheads into T7 libraries has also been reported.[5]

1,3-diketone and N-terminal peptide acyl hydrazine are known to react slowly in acid conditions to form N-acyl 1,2-pyrazole. The resulting N-acyl 1,2-pyrazole moiety is conveniently susceptible to attack by soft nucleophiles, such as thiol, resulting in departure of a leaving group (1,2-pyrazole). While replacement of the pyrazole moiety by variety of thiols is useful to produce thioesters for native chemical ligation (NCL), 1,2-pyrazoles which are stable to hydrolysis and any other form of destruction by nucleophiles present in biological media may be desirable.

A large body of reports confirm that linear aliphatic 1,3-diketones are long-term stable bio-orthogonal moieties.[6] There do not appear to be any proteins that bind to or react with 1,3-diketones, however, antibody uniquely reactive to 1,3-diketones were isolated from synthetic antibody libraries.[7-8] This work provided evidence for orthogonality of 1,3-diketo group: only a rare combination of peptide sequences inside an antibody binding site or in long 15-mer peptide have any detectable reactivity with this group. The small molecules with 1,3-diketone injected into blood circulation conjugate to the circulating anti-1,3-diketone antibody selectively.

There remains a need in the art for methods of producing genetically-encoded macrocycles with reactive groups that can be modified in benign aqueous conditions.

This background information is provided for the purpose of making known information believed by the applicant to be of possible relevance to the present invention. No admission is necessarily intended, nor should be construed, that any of the preceding information constitutes prior art against the present invention.

SUMMARY

The present invention relates to the synthesis of peptide macrocycles formed by cross-linking the peptide with a linchpin compound, and the demonstration that these macrocycles can be functionalized with diverse unnatural functionalities in benign conditions biocompatible with functionalization of phage-displayed libraries of peptides.

In one aspect, the invention may comprise a complex comprising a macrocyclic peptide construct formed by the reaction between (i) a polypeptide with two reactive groups X1 and X2; and (ii) a reactive compound comprising reactive groups Y1, Y2 and Z, which are capable of forming covalent bonds with said polypeptide such that:
X1 forms a bond by reaction with Y1; and
X2 forms a bond by reaction with Y2.

The polypeptide may be linked to a nucleic acid which encodes the polypeptide. The macrocyclic peptide comprises reactive group Z not originally present in the polypeptide. A pharmacophore or chemotype can then be formed by reacting Z with a suitable reactant.

The macrocyclic peptide bearing a pharmacophore can be formed in water in biologically-compatible conditions that leave the functional integrity of polypeptide, the encoding nucleic acid, phage, and/or the pharmacophore intact. Such conditions are referred to herein as "benign" conditions.

In some embodiments, X1 and X2 are thiol groups of cysteine side chains, and the reactive compound is one where Y1 and Y2 are both chloroalkane groups and Z is a diketone group, such as a 1,3 diketone. An exemplary reactive compound is 1,5-dichloropentanedion-2,4. The reaction between the reactive compound and a peptide produces an 1,3-diketone-containing macrocyclic polypeptide. In some embodiments, the polypeptide is attached or linked to a nucleic acid encoding the polypeptide. The macrocycle with a 1,3-diketone group (Z) can then be modified by reaction of said macrocycle with any molecule that contains, for example, an alkyl or aryl hydrazine group. The reaction of the macrocycle produces a pharmacophore or chemotype.

The invention also relates to a mixed library comprising two or more libraries of said peptides that each contain a silent DNA barcode which distinguishes between the two or more libraries on a genetic level, but which are phenotypically identical. For example, the silent DNA barcode may use the redundant genetic code to encode identical peptide linkers with different DNA sequences. Modification of these libraries with different pharmacophores produces a mixed library of different pharmacophores, in which any specific pharmacophore may be identified by the genetic barcode. Screening and sequencing of such libraries can identify either or both the peptide sequence and the pharmacophore, which may be critical for binding of polypeptide to a screening target.

In another aspect, the invention may comprise a method for constructing a macrocycle peptide library bearing a pharmacophore compound capable of bonding with a target substance arranged at a desired position in a random sequence. In some embodiments, the macrocycle peptide library may be produced from peptides with amino acids that have a section capable of bonding with a target substance arranged at a desired position in a macrocycle sequence. In some embodiments, the method comprises the steps of: (i) preparing a phage library of random peptides that comprise two cysteine residues; (ii) modifying the library with 1,5-dichloropentanedion-2,4 to produce a library of random macrocylic peptides bearing a diketone group; (iii) reacting the modified library with a pharmacophore having a hydrazine functionality, resulting in a library comprising a peptide macrocycle with a prescribed chemotype arranged in the random sequence.

In another aspect, the invention may comprise a mixed library comprising two or more macrocycle peptide libraries, each modified in a different manner and bearing an identifiable silent genetic barcode, and to methods of screening using the same.

In some embodiments, a diketone linchpin, such as 1,5-dichloropentanedion-2,4, can be used to modify peptides displayed on phage that contain DNA barcodes or silent barcode technology in the genome of the phage, as described in PCT WO 2016/061695 A1 "Genetic Encoding of Chemical Post-Translational Modifications for phage-displayed libraries". The resulting library of random macrocyclic peptides bearing a 1,3-diketone functionality can then be functionalized with diverse pharmacophores bearing a hydrazine functionality resulting in a library comprising a peptide macrocycle with a prescribed chemotype such that both peptide and the unnatural chemotype are encoded by DNA of the phage.

BRIEF DESCRIPTION OF THE FIGURES

For a better understanding of the present invention, as well as other aspects and further features thereof, reference may be made to the following drawings.

DETAILED DESCRIPTION

Unless defined otherwise, all technical and scientific terms used herein have the same meaning as commonly understood by one of ordinary skill in the art to which this invention belongs.

The production of genetically-encoded libraries, in which each library member is linked to an information template, such as DNA or RNA, makes it possible to process large chemical libraries without separating individual library members into individual solutions and reaction vessels. One can select target molecules from mixtures of genetically-encoded molecules and identify or amplify the selected molecule of interest using its information template.

One strategy for production of a library of cyclic peptides or display of peptides on phage, DNA or RNA is through the modification of a genetically encoded display of molecules derived from peptides modified with chemical (or enzymatic) post-translational modifications (cPTM). Typically, these methods use organic synthesis on the peptides to make peptide derivatives. It is known that an entire peptide library can be modified by uniform chemical modification. Selection from the modified library and sequencing of the DNA yields peptide sequences from which the modified peptide derivatives can be made. Several methods exist which involve conversion of libraries of peptides, libraries of phage-displayed polypeptides and libraries of RNA-displayed polypeptides to libraries of peptide derivatives.

Late-stage functionalization of unprotected peptides composed of natural amino acids in aqueous media provides a convenient approach to modify readily available million-to-billion scale genetically-encoded peptide libraries, phage-/mRNA/DNA-displayed, and expands the chemical space to incorporate unnatural chemotypes and pharmacophores not present in the original peptide libraries.

In some embodiments, the invention may comprise a two-step late-end functionalization of a linear peptide, which may provide several additional advantages not present in the prior art, including some or all of the following: (i) produce constructs of cyclic topology; (ii) a reactive intermediate is stable in storage conditions; (iii) permit plug-and-play functionalization with readily available hydrazines; and (iv) stability of the resulting bond to hydrolysis and exchange with excess of reactive group.

Figure 1:
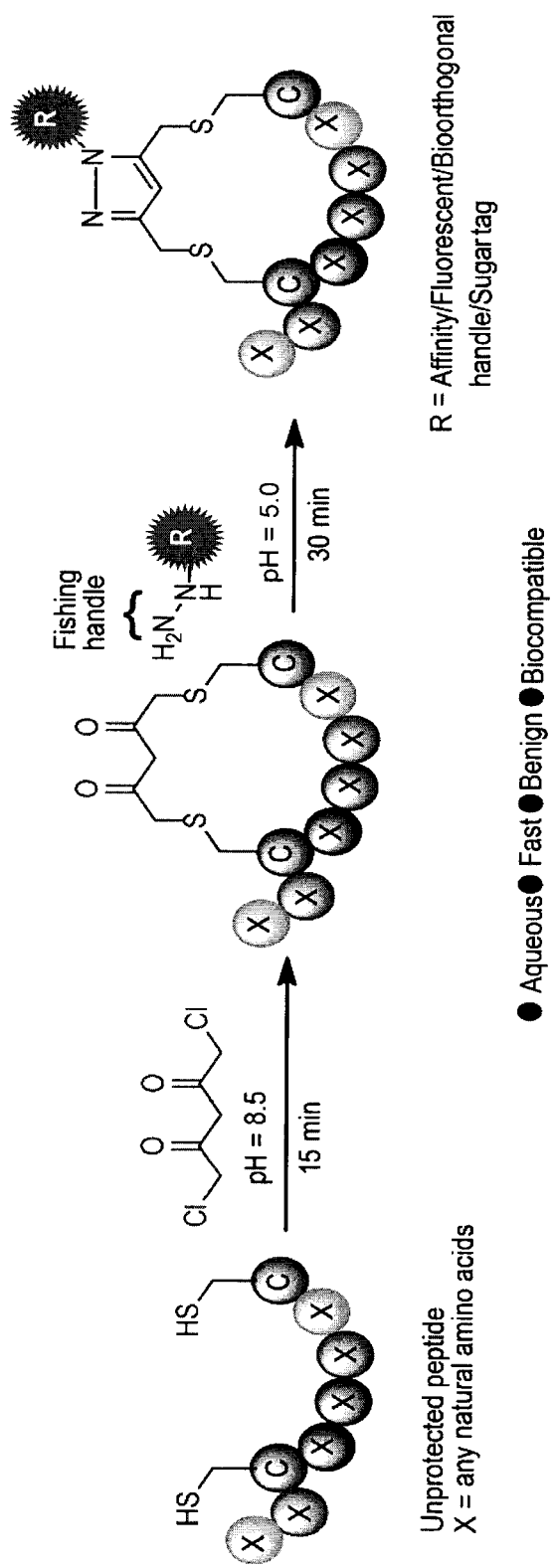
FIG. 1. Schematic depiction of one embodiment of a method of forming a macrocyclic peptide bearing a pharmacophore R.

In general terms, the method comprises a reaction between an unprotected peptide and a reactive compound to form a macrocyclic peptide, followed by modification of the macrocyclic peptide by a hydrazine, an example of which is shown schematically in FIG. 1. The second step modification introduces pharmacophore R to the construct.

As used herein, a "pharmacophore" is a part of a molecular structure that is responsible for a particular biological or pharmacological interaction that it undergoes. In one specific sense, it is an abstract description of a molecular feature or features that are necessary for molecular recognition of a ligand by a biological macromolecule. A "chemotype" means a grouping of compounds sharing a distinct chemical scaffold.

As used herein, a "macrocycle" or "macrocylic" compound is a molecular structure that contain one or more rings having 12 or more atoms. Macrocycles may combine the benefits of large biomolecules, such as high potency and selectivity, with those of small molecules, including reasonable manufacturing costs, favorable pharmacokinetic properties, including oral bioavailability, ease of administration and lack of immunogenicity.

It is known to adapt a dichloroacetone linchpin to convert a linear peptide to a cyclic structure and simultaneously introduce ketone functionality into the peptide library. However, post-functionalization of ketone-macrocycle was slow and required up to 24 hours of incubation in pH 4 conditions, which is incompatible with viability of phage.

As shown in FIG. 1, a linear peptide, preferably phage-displayed, may be any unprotected peptide having at least two reactive residues, such as two Cys residues. The peptide may comprise a $X_L Y X_M Y X_N$ structure, where X is any natural amino acid, Y is an amino acid with a reactive side-chain, L may be an integer from 2-20, M may be an integer from 2 to 10, and N may be zero or an integer from 1 to 20. Preferably, Y is cysteine. In one embodiment, the peptide is reacted to form a 1,3-diketone macrocyclic peptide (DKMP). The macrocycle is subsequently reacted, under benign aqueous conditions and in a short period of time, preferably less than about 2 hours and more preferably less than about 1 hour, with a hydrazine bearing a pharmacophore R.

As shown in FIG. 3, the alkylation of peptides with 1,5-dichloro-2,4-pentanedione (DPD) is a time sensitive reaction where an extra product with higher molecular mass than the desired diketone macrocyclic peptide (DKMP) is formed 30 minutes after starting the reaction. This additional product increases in ratio to the desired product with time and therefore the alkylation reaction is preferably quenched by dilution with water and purified, such as by HPLC, shortly, such as within 30 minutes, after starting the reaction to obtain the optimum yield of DKMPs.

The reaction between a substituted hydrazine and 1,3-diketone is known to occur under vigorous conditions, such as refluxing in toluene or ethanol. To the knowledge of the inventors, there are no reports that such a reaction can occur in benign aqueous solutions compatible with biological entities like bacteriophage and proteins, and complete in in relatively short period of time, such as one or two hours of incubation.

Therefore, in one aspect, the invention comprises the cycloaddition between a 1,3-diketone and aryl or alkyl hydrazine to form N-alkyl or N-aryl 1,2-pyrazole functionality. This reaction occurs within 120 minutes, and preferably less than about 60 minutes, and in benign aqueous conditions, such a pH 5 buffer and at ambient temperature, and produce a hydrolytically stable moiety.

As used herein, "benign aqueous conditions" means conditions which do not substantially damage a phage-displayed library of peptides and/or nucleic acids. The conditions may include moderate temperatures, for example, between about 5° and 30° C. and preferably between about 10° and 25° C., pH levels, for example, between about 3 to about 10, preferably between about 4 and 8, and more preferably between about 5 and 7, and the substantial absence of damaging reactants, solvents, catalysts and/or metal ions, such as transition metal ions which are redox catalysts. In this sense, "substantial" means that some minor damage may occur, but any such damage does not impair the functionality of the resulting macrocycle or the viability of phage.

Many methods for one-step functionalization of linear peptide libraries exist. N-terminal conjugation is known, using ligation of oximes, 2-amino benzamidoxime, and a Wittig reaction with N-terminal aldehydes. Michal addition to dehydroalanines to form linear glycopeptides may be used. Boroxazole functionalities may be introduced into commercially available phage displayed PhD C7C library by alkylation of both Cys. A similar Cys-alkylation may be used to introduce non-covalent and covalent warheads into T7 libraries.

1,3-diketones are known to react with sulfenic acid—a transient species formed from endogenous cysteines due to oxidative stress—via attack of sulfenic acid by nucleophilic carbon of 1,3-diketone. Such reactions occur preferentially with cyclic 1,3 diketones such as dimedone and are known to be slow with linear 1,3 diketones. To the knowledge of the inventors, 1,3-diketones are bona fide bioorthogonal reagents with long-term stability in diverse range of biological media.

Where the diketone is phage-displayed, some hydrazine derivatives cause toxicity to phage leading to substantial elimination of infective phage particles. In some embodiments, the addition of a metal chelator, such as methylglycinediacetic acid (MGDA) ethylenediaminetetraacetic acid (EDTA), or nitriloacetic acid (NTA) may mitigate the toxicity. For example, EDTA used at concentrations of 1-2 mM does not influence the rate of reaction between diketone and hydrazine but does rescue the toxicity.

In one aspect, the invention may comprise a mixed library comprising two or more libraries of peptides that each contain a silent genetic barcode which distinguishes between the two or more libraries on a genetic level, but which are phenotypically identical. For example, the silent genetic barcode may use the redundant genetic code to encode identical peptide linkers with different DNA sequences. Each library may be modified with different pharmacophores and combined to produce the mixed library of different pharmacophores, in which any specific pharmacophore may be identified by the genetic barcode. Screening and sequencing of such libraries can identify either or both the peptide sequence and the pharmacophore, which may be critical for binding of polypeptide to a screening target.

The production of peptides displayed on phage that contain DNA barcodes or silent barcode technology in the genome of the phage, is described in PCT WO 2016/061695 A1 "Genetic Encoding of Chemical Post-Translational Modifications for phage-displayed libraries", the entire contents of which are incorporated herein by reference, where permitted.

In another aspect, the invention comprises a method for constructing a macrocycle peptide library bearing a pharmacophore compound capable of bonding or interacting with a target, wherein the pharmacophore is arranged at a different positions in a random sequence. In some embodiments, the macrocycle peptide library may be produced from peptides with amino acids that have a section capable of bonding with a target substance arranged at a desired position in a macrocycle sequence. In some embodiments, the method comprises the steps of: (i) preparing a phage library of random peptides that comprise two cysteine residues; (ii) modifying the library with a diketone linchpin, such as 1,5-dichloropentanedion-2,4, to produce a library of random macrocyclic peptides bearing a diketone group; (iii) reacting the modified library with a pharmacophore having a hydrazine functionality, resulting in a library comprising a peptide macrocycle with a prescribed pharmacophore arranged randomly in the sequence.

In some embodiments, a diketone linchpin, such as 1,5-dichloropentanedion-2,4, can be used to modify peptides displayed on phage that contain DNA barcodes or silent barcode technology in the genome of the phage, as described in PCT WO 2016/061695 A1 "Genetic Encoding of Chemical Post-Translational Modifications for phage-displayed libraries". The resulting library of random macrocyclic peptides bearing a 1,3-diketone functionality can then be functionalized with diverse pharmacophores bearing a hydrazine functionality resulting in a library comprising a peptide macrocycle with a prescribed chemotype such that both peptide and the unnatural chemotype are encoded by DNA of the phage.

In another aspect, the invention may comprise a mixed library comprising two or more macrocycle peptide libraries, each functionalized in a two-step method as described herein, to comprise a different pharmacophore or chemotype, and bearing a silent genetic barcode, and to methods of screening using the same against a target.

EXAMPLES

To gain a better understanding of the invention described herein, the following examples are set forth. It should be understood that these examples are for illustrative purposes only. Therefore, they should not limit the scope of the claimed invention in any way.

1,5-dichloro-2,4-pentanedione (DPD) was synthesized according to a previously published protocol and the identity of the synthesized product was verified by single crystal X-ray structure.

DPD was used to modify synthetic peptides of $X_LCX_MCX_N$ structure to form 1,3-diketo functionalized peptide macrocycles. X is any natural amino acid, L may be an integer from 2-20, M may be an integer from 2 to 10, and N may be zero or an integer from 1 to 20. M was varied from 2 to 10 to show that neither cyclization nor subsequent hydrazine ligation have neither upper nor lower limit on ring size and, thus, DPD is similar to a,a'-metabromoxylene, DFS, dichlorotetrazine, and other bis-electrophiles reported to form both small and larger macrocycles.

DPD robustly and reproducibly modified five peptides of structure of $X_LCX_MC$, where X, L and M are as above, as shown in FIG. 2A, to produce 1,3-diketone modified macrocyclic peptides (DKMPs). Reactions exhibited quantitative conversion within 60 min.

These 1,3-diketone macrocyclic peptides can be quantitatively ligated to aryl or alky hydrazine functionality to form N-alkyl or N-aryl 1,2-diazole within 60 minutes at pH 5.0 as confirmed by LCMS.

We conducted investigation of reactivity between various hydrazides and a macrocycle derived from peptide SWCDYRC because it conveniently includes all potentially problematic reactive residues (primary N-terminal amine with pKa of 7, carboxylic acid, phenol, guanidine, indol). Investigations determining reactions rates and product yields were conducted on peptide SQCVRSC, due to its high solubility in water and the clear difference in HPLC retention time between the DKMP and 12,-diazol product.

To show generality of conjugation, we modified five diketo-macrocycles (FIG. 2A) with up to twelve different alkyl or aryl hydrazines (FIGS. 2B and 2C), including phenyl-, 4-methylphenyl, 4-nitrophenyl, 4-fluorophenyl, pentafluorophenyl, methyl, hydroxyethyl, ethyl, manosyl, propargyl, biotinyl, fluoresceinyl hydrazine and hydrazine itself.

Figure 2:
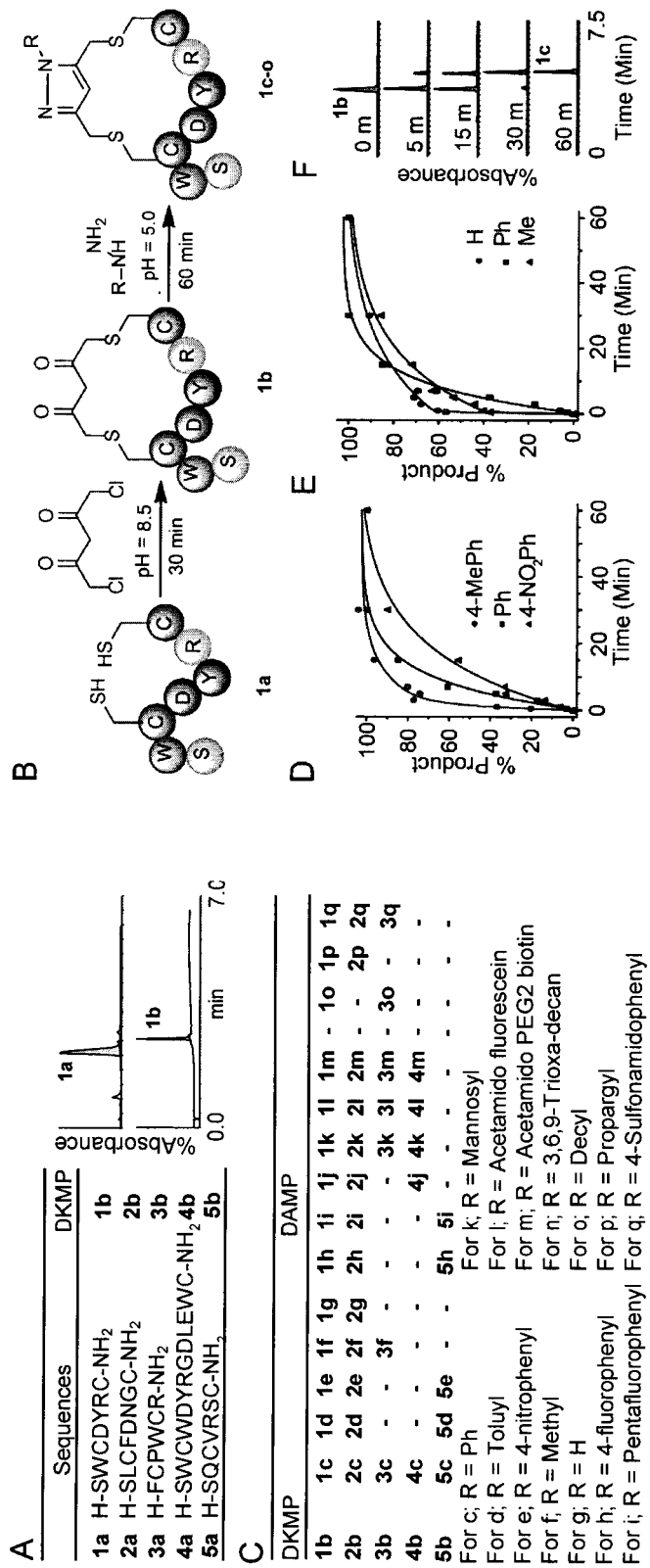
FIG. 2. (a) The sequences of peptides studied in reaction with 1,5-dichloro-2,4-pentanedione (DPD) and their macrocyclic products that contain 1,3-diketone. Examples of LCMS traces for the conversion peptide to macrocyclic peptides. (B) Alkylation of peptide SWCDYRC with DPD and subsequent ligation of aryl hydrazines or alkyl hydrazines. (C) The examples of the reactions performed between di-ketone macrocyclic peptides (DKMP) and a variety of alkyl and aryl hydrazines to form diazole macrocyclic peptides (DAMP). (D) and (E) Rates of modification of 1,3-diketone macrocyclic peptides with aryl hydrazines showing modest substituent effect (unsubstituted>alkyl>aryl) and through ring effect in Hammett series with negative rho value indicating a buildup of positive charge in transition state of the rate-determining step. (F) shows time dependent LCMS trace for the formation of 1,2-diazole from 1,3-diketone macrocycle.

FIG. 2. Panel A shows schematically the sequences of five peptides studied in reaction with 1,5-dichloro-2,4-pentanedione (DPD) and designations of the five peptides as 1a-4a, and their macrocyclic products, termed 1,3-diketone macrocyclic peptides (DKMP), after reaction with DPD as 1b-4b. The same panel shows examples of HPLC traces for the conversion peptide 1a to DKMP 1b. Panel B shows schematically the alkylation of peptide SWCDYRC with DPD to form DKMP and subsequent ligation of DKMP with aryl hydrazines or alkyl hydrazines. Panel C lists the examples of reactions performed between diketone macrocycles and variety of alkyl and aryl hydrazines. Panel D shows representative rates of formation of products 1c-g from 1b and aryl hydrazines. Formation of 1,2-diazole exhibits modest substituent effect (unsubstituted>alkyl>aryl) and through ring effect. Panel E shows representative rates of formation of 1,2 diazoles from DKMP and hydrazine, alkyl hydrazine and aryl hydrazine. Panel F shows time dependent HPLC trace for the formation 1c from 1b.

Although conversion of diketone to pyrazole involves at least 4 reactions (addition, dehydration, second addition, second dehydration) and distinct intermediates, none of these intermediates were observed throughout the course of the reaction by LCMS except for, in the reaction between 1,3 diketone and benzoyl hydrazine. In the latter case, only the formation of the intermediate was observed and this intermediate did not undergo the final addition or dehydration steps.

To see if there any electronic factor involves in the pyrazole formation, we tested three different 4-substituted phenylhydrazines ($CH_3$, H and $NO_2$), and found that para electron donating substituent accelerated the pyrazole formation whereas para electron withdrawing substituent decreased the rate of the pyrazole formation (see FIG. 2D).

Figure 3A:
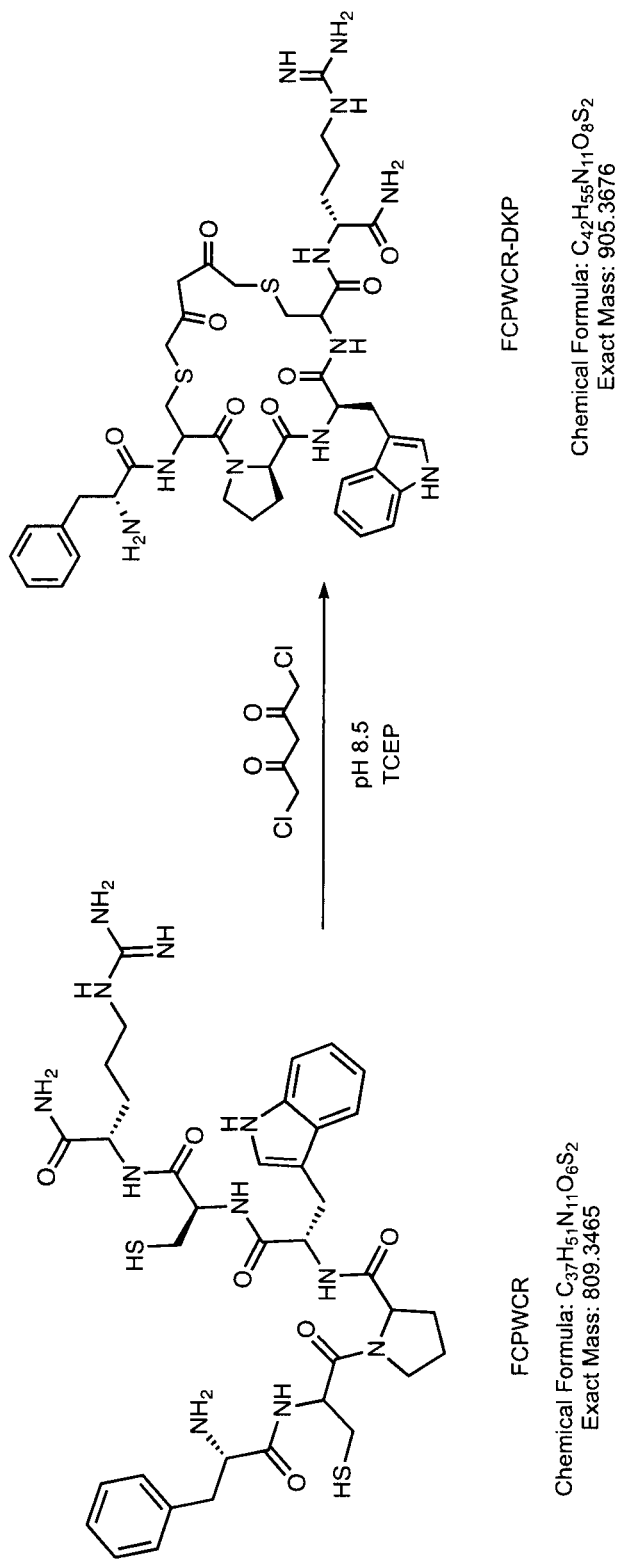
FIGS. 3A and 3B. The alkylation reaction with 1,5-dichloro-2,4-pentanedione (DPD) is time-sensitive as it forms an additional product with higher molecular weight than the desired di-ketone macrocyclic peptide (DKMP), which increases in ration over time.
Figure 3B:
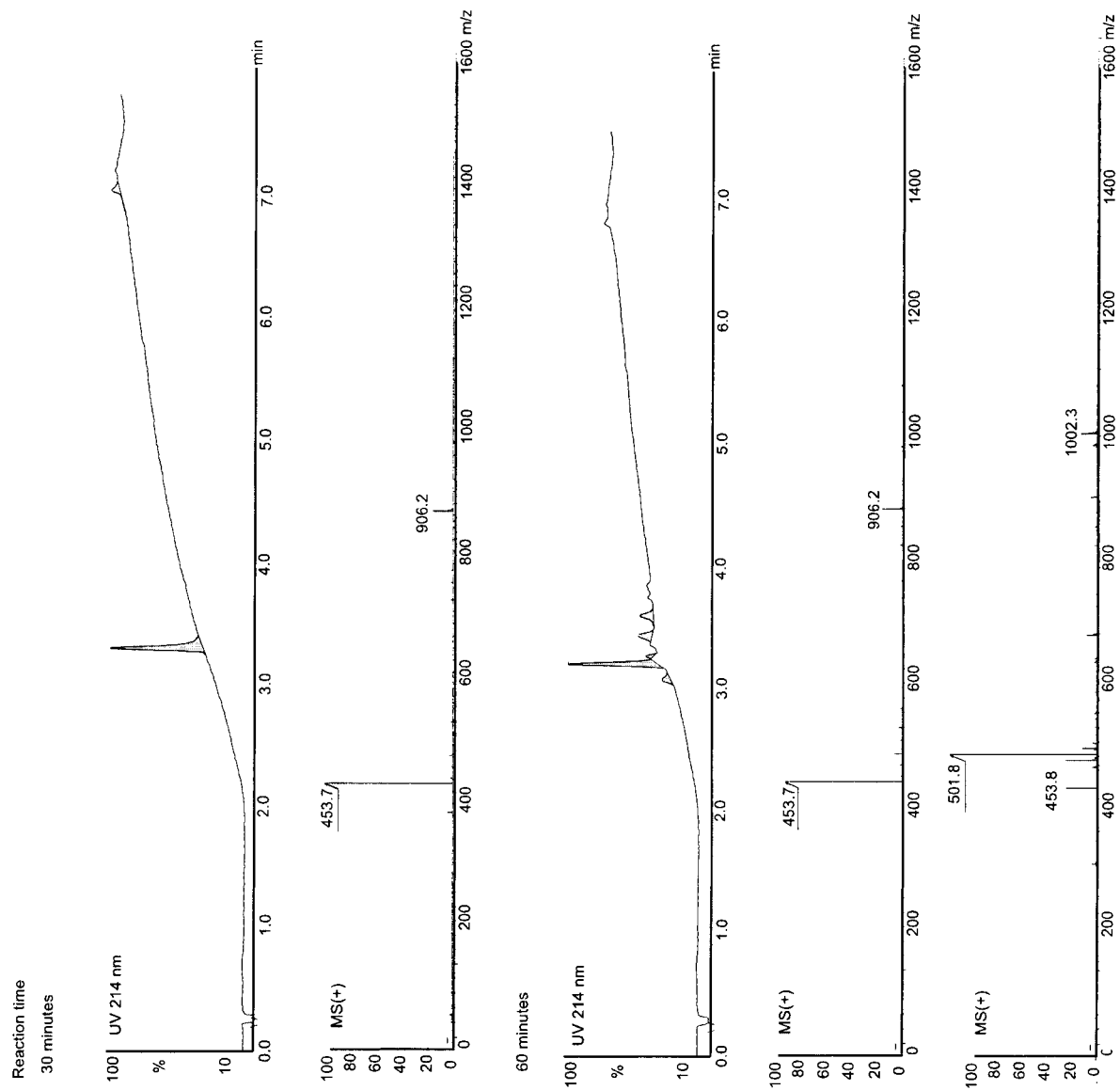

FIGS. 3A and 3B shows a typical reaction between peptide and DPD that generates a product with increase of mass of 96 units; interestingly, upon prolonged incubation between peptide and DPD (60 min trace in 3B) we observed a consistent generation of side products with additional mass of 96 units (formally, reaction of product with another DPD unit). The identity of this new side-products is presently unknown but this product no longer contains reactive diketo functionality and therefore cannot react with hydrazine.

Figure 4A:
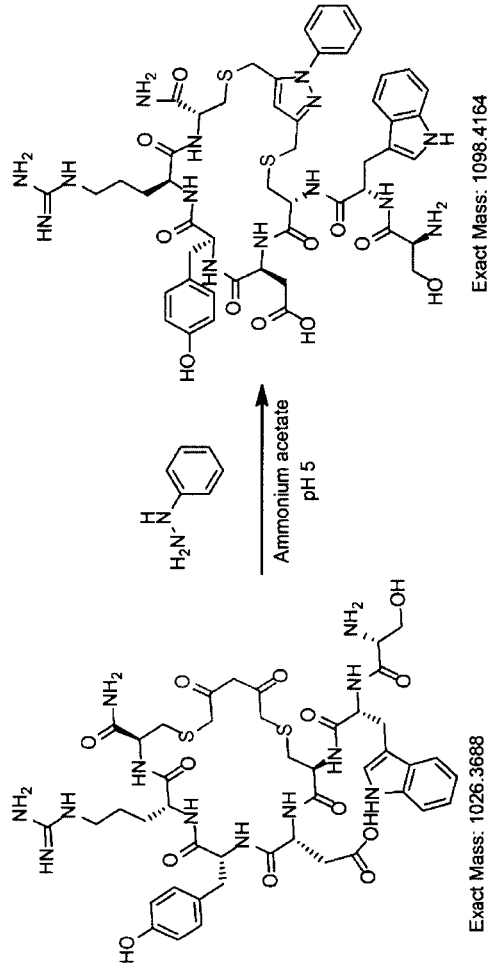
FIGS. 4A and 4B. Liquid Chromatography-mass spectrometry (LCMS) traces describing formation of 1,2-diazole macrocyclic peptides from aryl hydrazines displaying different pharmacophores.
Figure 4A:
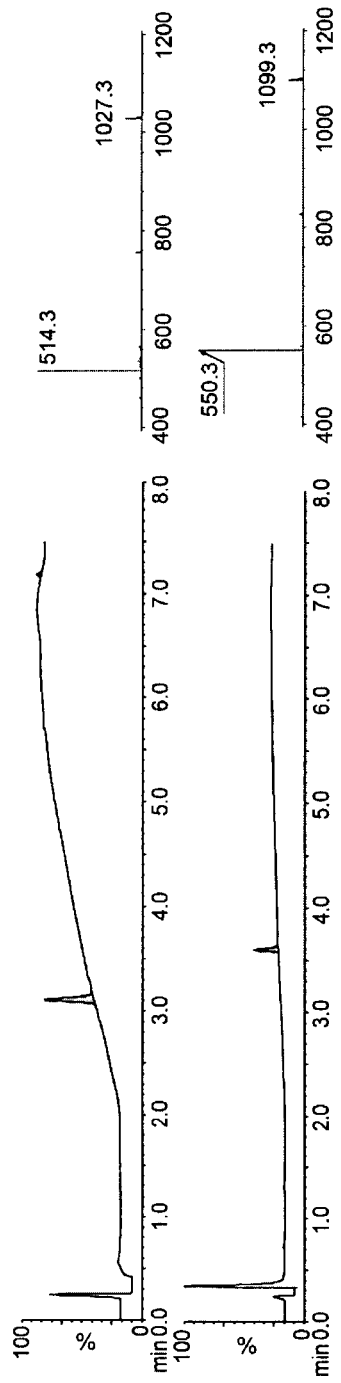
Figure 4B:
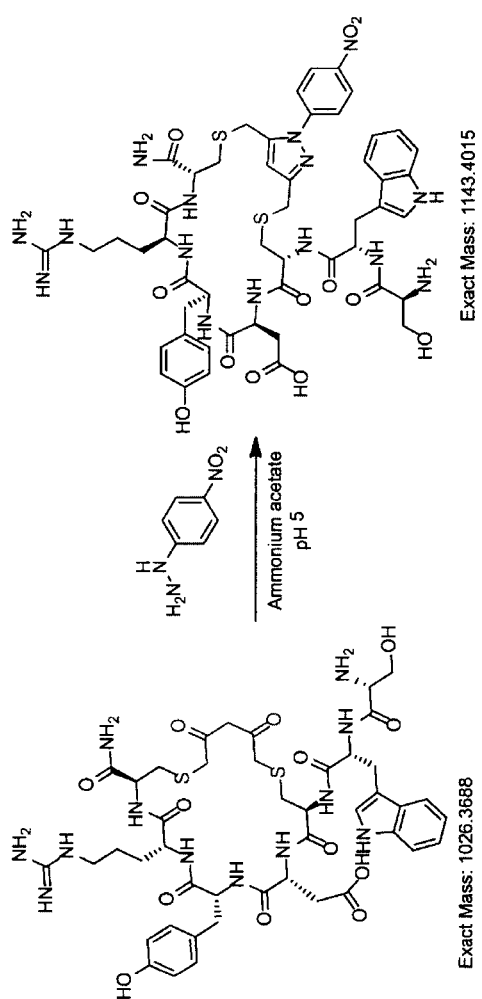
Figure 4B:
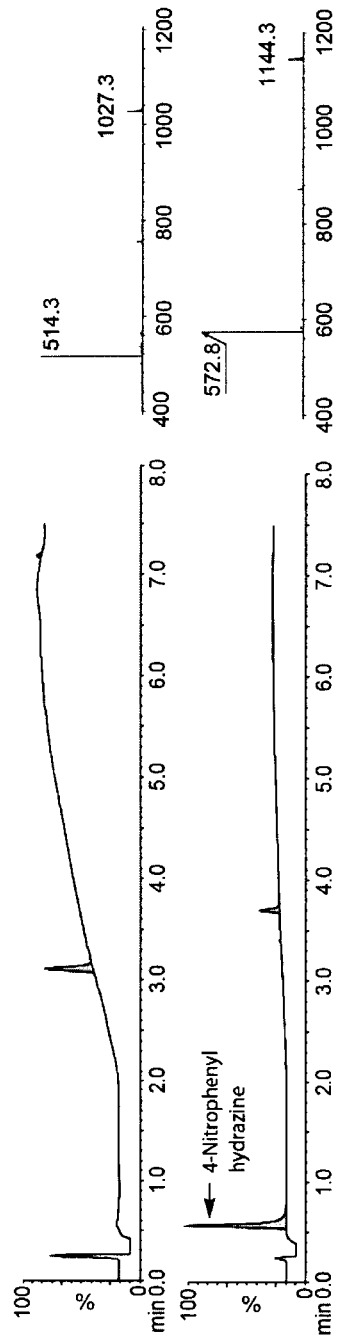

FIGS. 4A and 4B shows typical LCMS traces used to monitor the efficiency of the reaction and its kinetics.

Figure 5A:
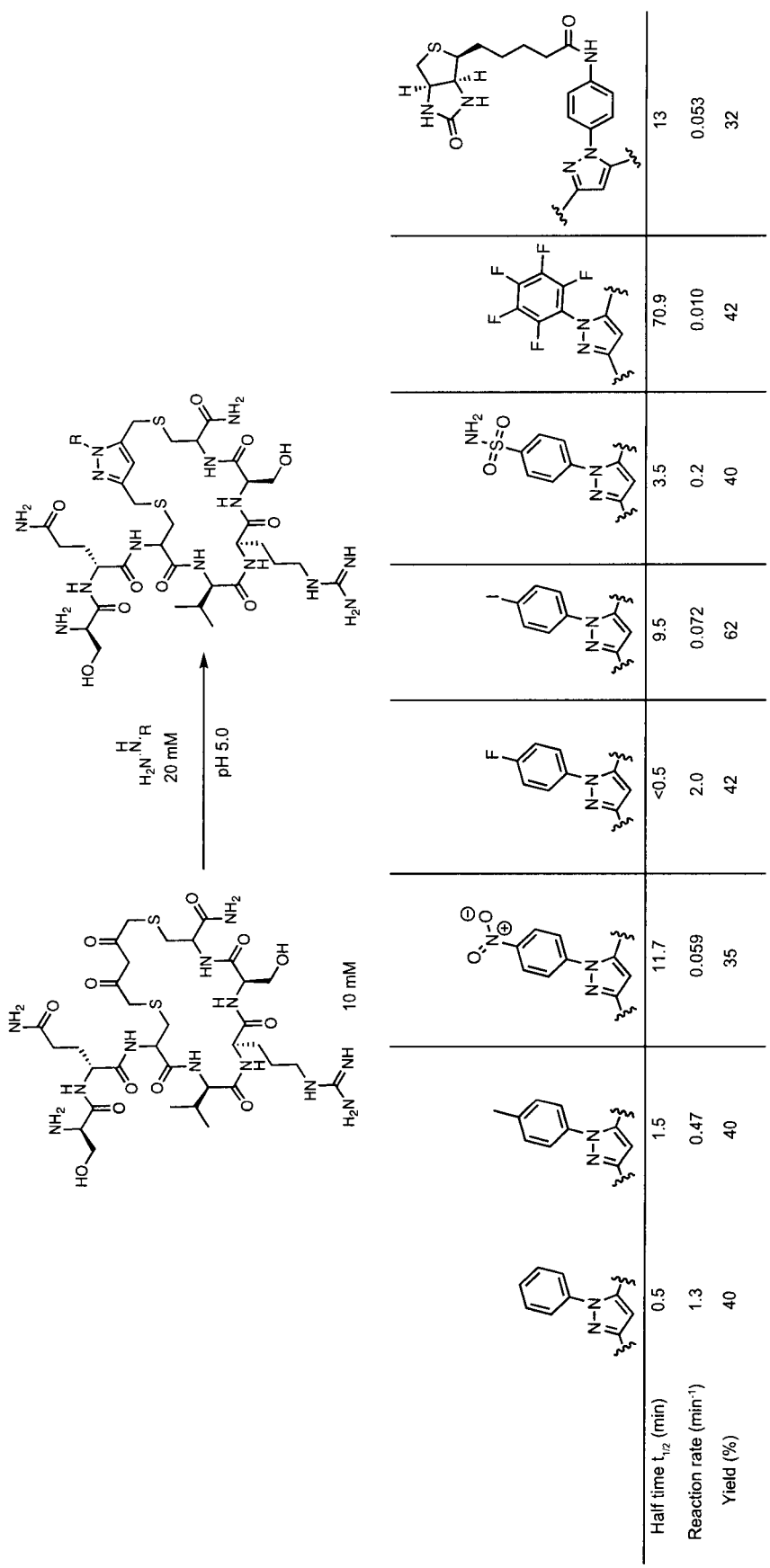
FIGS. 5A and 5B. Calculated reaction rates and product yields for different hydrazine analogs with the same DKMP and phenyl hydrazine with different DKMPs.
Figure 5B:
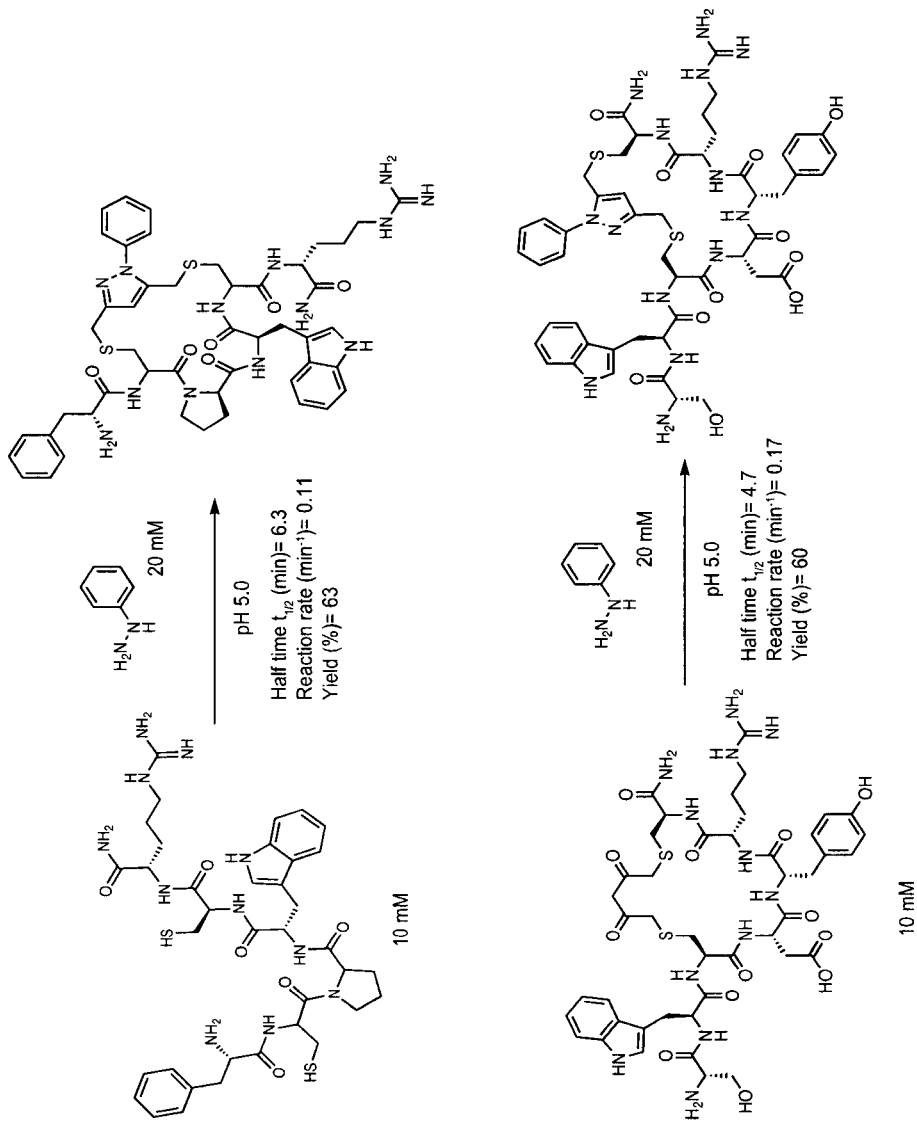

FIG. 5A shows reactions of DKMP derived from peptide sequence SQCVRSC (10 mM) with 20 mM solution of eight different hydrazines. The rate of the reaction and it 50% completion ($t_{1/2}$) depended on the electronic properties of the substituent on the hydrazine. For example, electron poor pentafluorophenyl hydrazine had one of the slowest conversion rates and longest $t_{1/2}$. Para-nitro, para-sulfonamide and para-amide groups that deactivate the aromatic ring decreased the reaction rates when compared to unsubstituted phenyl. While there were no visible side products or unreacted starting material according to LCMS traces, the isolated yields for various products of DKMP and hydrazine reactions ranged from 30-60% (See FIG. 5A and 5B). In addition to SWCDYRC peptide, two other peptides FCPWCR and SQCVRSC were also chosen to test the rates of the reaction between 10 mM of the DKMP and 20 mM hydrazine. The rates depended on the sequence of the peptide, indicating the non-obvious relationships between the peptide sequence and the rate of the reaction.

EXAMPLE 2: Stability of the 1,2 diazoles conjugates. Crossover experiments were carried out by incubating one DKMP with 60 equivalent excess of methyl hydrazine in ammonium acetate buffer (pH=4.6). The results showed that no crossover product was found, even after 2 weeks. Unlike published N-acyl pyrazole-peptides, and previously known peptide hydrazide-conjugates susceptible to hydrolysis or reversion of conjugation in acidic conditions, N-alkyl or N-aryl 1,2-diazole peptide macrocycles are stable both to loss of hydrazine functionality in the presence of or excess of hydrazine.

Figure 6:
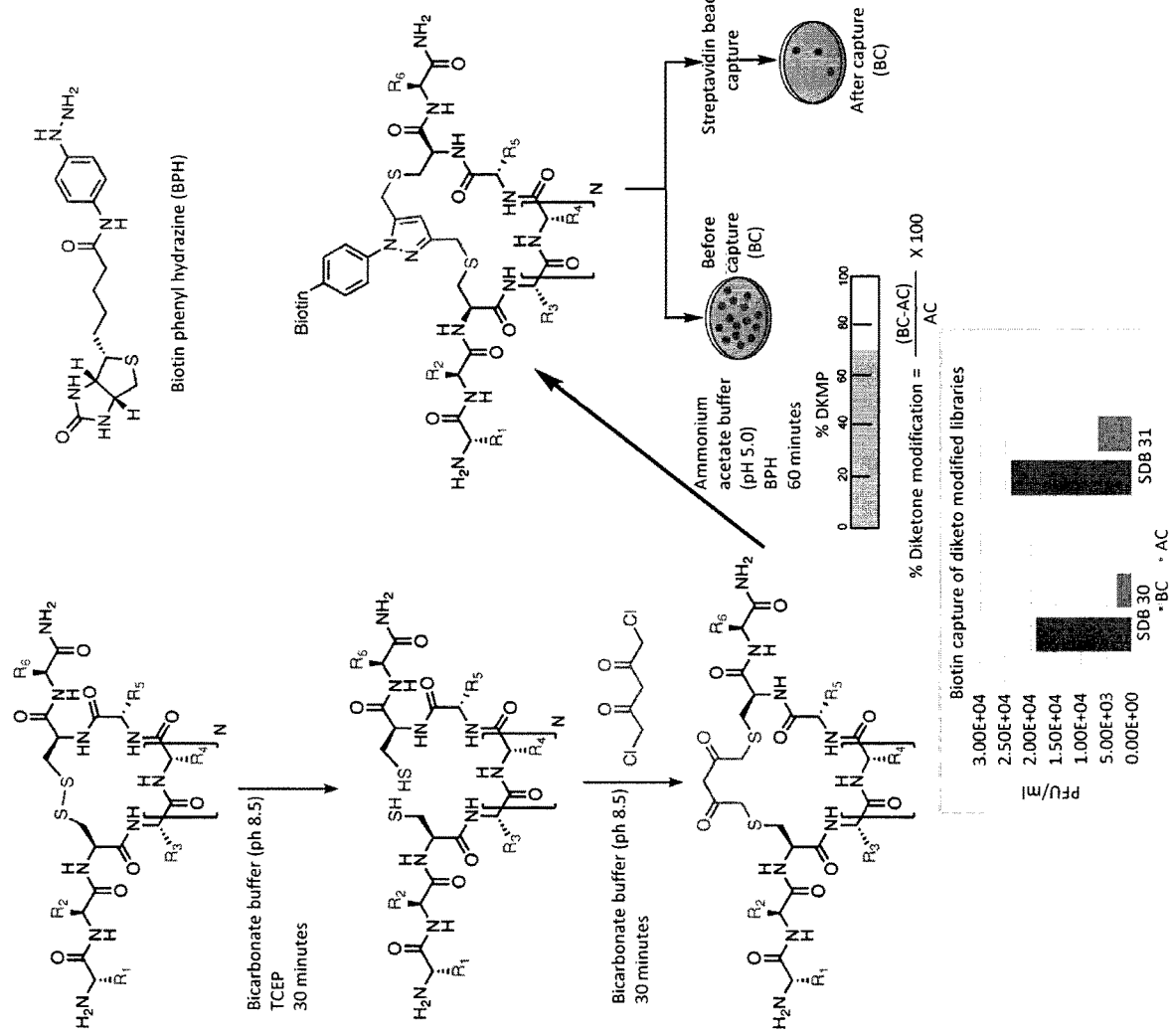
FIG. 6. Modification of phage displayed peptides with DPD and quantification of this modification using biotin capture FIG. 7. Modification of two phage libraries displaying peptides and silent DNA barcodes with DPD and two different chemotypes produces a mixed library in which the two chemotypes are encoded by silent DNA barcodes.

EXAMPLE 3: Modification of phage displayed libraries by DPD and subsequent modification to form 1,2 diazoles. Phage-displayed library of peptides can be modified with DPD, and post-functionalized with hydrazines. Biotin capture demonstrated that more than 60% of the DPD-modified library is biotinylated with biotin-hydrazine (See FIG. 6). Even when stored at 4° C. for several days, diketone-phage remains reactive to biotinyl hydrazine; showing that late stage functionalization can be done any time after storage.

In the reaction between phage diketone and hydrazine, some hydrazine derivatives cause toxicity to phage, leading to elimination of >99.999% of infective phage particles in less than 5 minutes (as determined by plaque forming assay). For example, treating phage with 2 mM phenyl hydrazine for 2 minutes decreased the number of infective particles from $10^5$ to zero. The source and mechanism of toxicity was not obvious and was difficult to systematize: it depended on the concentration of hydrazine and its nature, as well as some sporadic factors (preparation of solution). Toxicity dependence on concentration of hydrazine was not linear. In many cases, hydrazine was lethal to phage eliminating all infective particles before the reaction was completed. We discovered that addition of metal chelator such as EDTA at concentrations of 1-2 mM did not influence the rate of reaction between diketone and hydrazine but it rescued the toxicity. For example, in the presence of 1 to 2 mM EDTA and 2 to 20 mM phenyl hydrazine, phage did not show any significant decrease in the number of infective particles for several hours. Optimal location conditions between phage-diketone and hydrazine derivatives are in the presence of 1-2 mM metal chelator such as EDTA.

Figure 7:
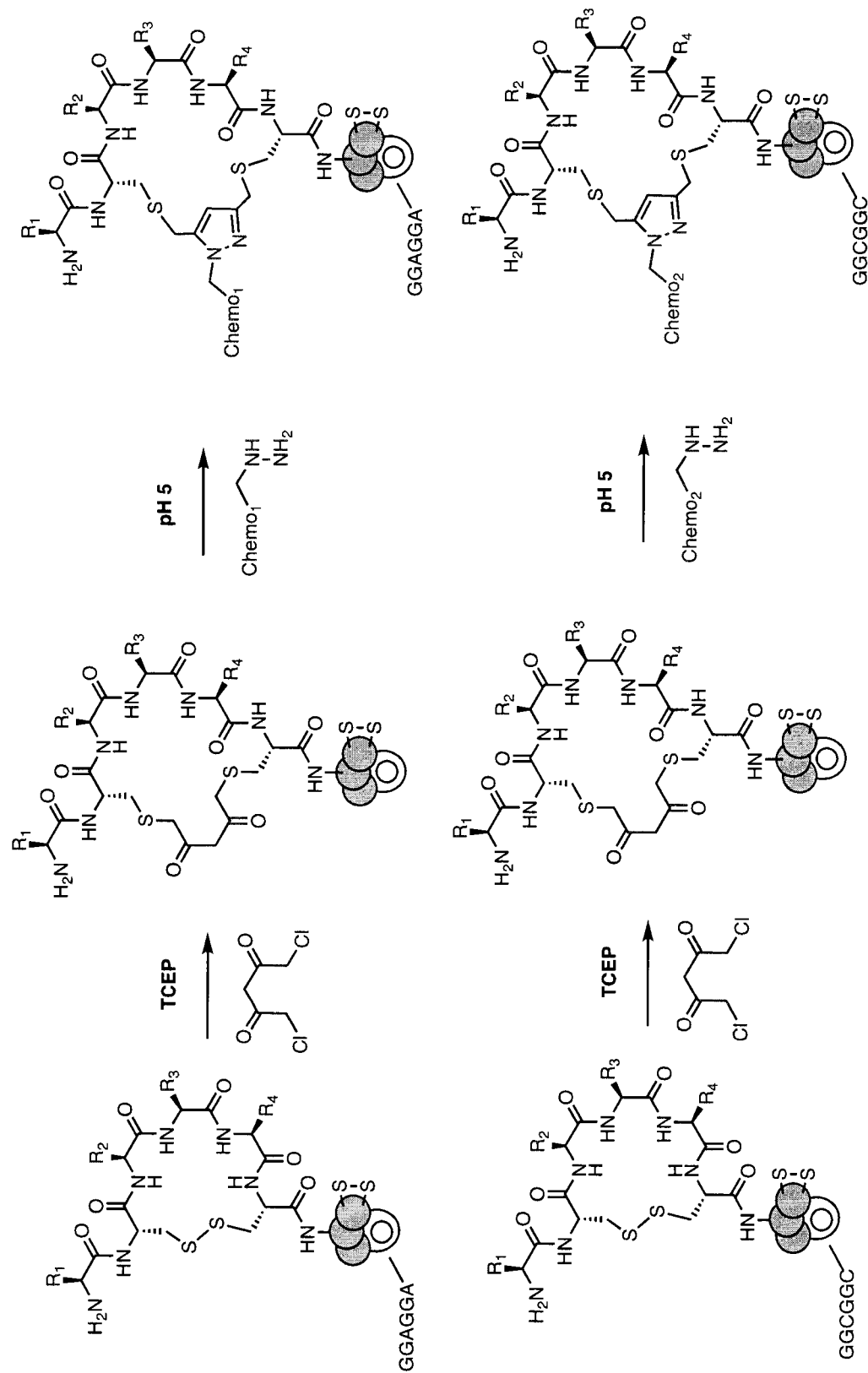

EXAMPLE 3: Two phage libraries displaying peptides and silent DNA barcodes modified with DPD and separately with two different hydrazine containing chemotypes (Chemo1 and Chemo2) produces a mixed library in which the two chemotypes are encoded and identifiable by the silent DNA barcodes (See FIG. 7). The mixed library may be used to biopan for macrocyclic peptide chemotypes which bind to a selected target.

Definitions and Interpretation

The description of the present invention has been presented for purposes of illustration and description, but it is not intended to be exhaustive or limited to the invention in the form disclosed. Many modifications and variations will be apparent to those of ordinary skill in the art without departing from the scope and spirit of the invention. Embodiments were chosen and described in order to best explain the principles of the invention and the practical application, and to enable others of ordinary skill in the art to understand the invention for various embodiments with various modifications as are suited to the particular use contemplated.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such aspect, feature, structure, or characteristic with other embodiments, whether or not explicitly described. In other words, any element or feature may be combined with any other element or feature in different embodiments, unless there is an obvious or inherent incompatibility between the two, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated.

As will be understood by the skilled artisan, all numbers, including those expressing quantities of reagents or ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, as used in an explicit negative limitation.

REFERENCES

All publications, patents and patent applications mentioned in this Specification are indicative of the level of skill of those skilled in the art to which this invention pertains and are herein incorporated by reference to the same extent as if each individual publication, patent, or patent applications was specifically and individually indicated to be incorporated by reference.

(1) Franzini, R. M.; Neri, D.; Scheuermann, J. DNA-Encoded Chemical Libraries: Advancing beyond Conventional Small-Molecule Libraries *Accounts of Chemical Research* 2014, 47, 1247-1255.

(2) Assem, N.; Ferreira, D. J.; Wolan, D. W.; Dawson, P. E. Acetone-Linked Peptides: A Convergent Approach for Peptide Macrocyclization and Labeling *Angewandte Chemie International Edition* 2015, 54, 8665-8668.

(3) Ng, S.; Derda, R. Phage-displayed macrocyclic glycopeptide libraries *Organic & Biomolecular Chemistry* 2016, 14, 5539-5545.

(4) McCarthy, K. A.; Kelly, M. A.; Li, K.; Cambray, S.; Hosseini, A. S.; van Opijnen, T.; Gao, J. Phage Display of Dynamic Covalent Binding Motifs Enables Facile Development of Targeted Antibiotics *Journal of the American Chemical Society* 2018, 140, 6137-6145.

(5) Uematsu, S.; Tabuchi, Y.; Ito, Y.; Taki, M. Combinatorially Screened Peptide as Targeted Covalent Binder: Alteration of Bait-Conjugated Peptide to Reactive Modifier *Bioconjugate Chemistry* 2018, 29, 1866-1871.

(6) Gupta, V.; Paritala, H.; Carroll, K. S. Reactivity, Selectivity, and Stability in Sulfenic Acid Detection: A Comparative Study of Nucleophilic and Electrophilic Probes *Bioconjugate Chemistry* 2016, 27, 1411-1418.

(7) Rader, C.; Turner, J. M.; Heine, A.; Shabat, D.; Sinha, S. C.; Wilson, I. A.; Lerner, R. A.; Barbas, C. F. A Humanized Aldolase Antibody for Selective Chemotherapy and Adaptor Immunotherapy *Journal of Molecular Biology* 2003, 332, 889-899.

(8) Barbas, C. F.; Kang, A. S.; Lerner, R. A.; Benkovic, S. J. Assembly of combinatorial antibody libraries on phage surfaces: the gene III site *Proceedings of the National Academy of Sciences* 1991, 88, 7978-7982.

The invention claimed is:

1. A macrocyclic polypeptide comprising a linear peptide portion comprising $X_L CysX_M CysX_N$, where X is any natural amino acid, L is an integer from 2-20, M is an integer from 2 to 10, and N is zero or an integer from 1 to 20, and a diazole moiety formed from the reaction between a diketone linchpin and the cysteine residues and a subsequent reaction with an alkyl or aryl hydrazine, wherein the diazole moiety bears a pharmacophore.

2. The polypeptide of claim 1, wherein the polypeptide is genetically encoded by and linked to a nucleic acid.

3. A mixed peptide library comprising two or more libraries, each comprising a plurality of polypeptides as claimed in claim 1, wherein each library comprises a silent genetic barcode which distinguishes between the two or more libraries on a genetic level, but which are phenotypically identical, and each library has been separately modified with a different pharmacophore.

4. The mixed peptide library of claim 3 which is a phage library.

5. A method of identifying a pharmacophore with specificity to a target, comprising screening the mixed library of claim 3 with the target.

6. The polypeptide of claim 1, wherein the subsequent reaction is with an alkyl hydrazine.

7. The polypeptide of claim 1, wherein the subsequent reaction is with an aryl hydrazine.

* * * * *